United States Patent
Aves

(10) Patent No.: US 6,554,809 B2
(45) Date of Patent: Apr. 29, 2003

(54) EPIDURAL CATHETER NEEDLE

(76) Inventor: Teodulo Aves, 8722 Dallam Ct., Houston, TX (US) 77064-8611

( * ) Notice: Subject to any disclaimer, the term of this patent is extended or adjusted under 35 U.S.C. 154(b) by 0 days.

(21) Appl. No.: 09/921,179

(22) Filed: Aug. 2, 2001

(65) Prior Publication Data

US 2003/0028146 A1 Feb. 6, 2003

(51) Int. Cl.7 ............................................. A61M 5/32
(52) U.S. Cl. ...................................................... 604/272
(58) Field of Search .............................. 604/272–274, 604/264, 93.01, 158–160, 164.01, 164.06, 164.07, 164.09, 164.1, 164.11, 164.13, 165.01, 165.02, 166.01, 170.01, 170.02, 170.03, 171, 43–44, 523, 524

(56) References Cited

U.S. PATENT DOCUMENTS

| | | | |
|---|---|---|---|
| 4,141,365 A | 2/1979 | Fischell et al. ............ | 128/404 |
| 4,721,506 A | 1/1988 | Teves ......................... | 604/51 |
| 4,781,691 A * | 11/1988 | Gross ......................... | 604/164 |
| 4,808,157 A | 2/1989 | Coombs ...................... | 604/44 |
| 5,425,717 A | 6/1995 | Mohiuddin ................. | 604/160 |
| 5,573,519 A | 11/1996 | Zohmann .................... | 604/272 |
| 5,628,734 A | 5/1997 | Hatfalvi ...................... | 604/272 |
| 5,843,048 A | 12/1998 | Gross ......................... | 604/264 |
| 5,848,996 A | 12/1998 | Eldor ......................... | 604/272 |
| 6,283,948 B1 * | 9/2001 | McKernan et al. ......... | 604/272 |

\* cited by examiner

*Primary Examiner*—Anhtuan T. Nguyen
*Assistant Examiner*—Ann Y Lam
(74) *Attorney, Agent, or Firm*—Rosenthal & Osha L.L.P.

(57) ABSTRACT

A needle comprising a hollow shaft having opposed distal and proximal ends, the hollow shaft having a lumen extending from the proximal end of the shaft and terminating at an opening on a top of and proximal to the distal end of the needle shaft. A cutting surface is at the distal end of the hollow shaft adapted to be inserted into a patient, wherein the cutting surface is on the bottom of the distal end of the hollow shaft.

20 Claims, 5 Drawing Sheets

EPIDURAL CATHETER NEEDLE

BACKGROUND OF INVENTION

1. Field of the Invention

The invention relates generally to the field of epidural needles and methods of using the same.

2. Background Art

In general there are two methods for administering epidural anesthesia. The first is by means of a straight epidural needle connected at its proximal end to a syringe or other source of liquid anesthesia. The second is by means of a curved-tip epidural needle used to introduce an epidural catheter into the epidural space, which ranges on the order of 2–7 mm in width.

Straight epidural needles employed in the former procedure do not require the passage of a catheter. They typically have a straight distal end and a gauge size on the order of 21–22 gauge (iso-9626). Curved-tip epidural needles, through which a catheter is introduced, of necessity are somewhat larger, having a gauge size typically on the order of 17–18 gauge (iso-9626).

Curved-tip epidural needles, used for introducing a catheter into the epidural space, possess a curved tip so that the distal end of the catheter can curve upward for proper placement within the epidural space, rather than perpendicularly abutting the dura matter, the delicate membrane lying over the arachnoid and pia matter covering the spinal cord.

The epidural needles of the curved type currently in use are of two kinds: (1) those curved to have an inclined surface on the order of 7° from the longitudinal axis (known as "Tuohy" epidural needles); and (2) those curved to have an inclined surface on the order of 12° from the longitudinal axis (known as "Husted" epidural needles.)

Whether the procedure is of the type wherein the anesthesia is introduced through a syringe attached to the epidural needle or of the type where the anesthesia is introduced through a catheter, great care must be taken to avoid puncturing the dura mater and thus permitting spinal fluid to leak out.

In a typical procedure, a local anasthetic may first be given to minimize pain and discomfort from the epidural needle. With the stylet in the needle, the needle is slowly and carefully inserted until it abuts the ligamentum flavum, at which time the anesthesiologist senses an increase of resistance to further insertion. At this time, the stylet is removed from the needle and a "loss of resistance" syringe is attached to the luer fitting of the needle hub. By slowly advancing the needle and syringe while simultaneously applying pressure to the syringe piston, the ligamentum flavum is penetrated and the needle is advanced into the epidural space where loss of resistance to the syringe piston is confirmed.

At this point, the syringe is removed and the epidural catheter is inserted through the needle until the distal end of the catheter exits the curved tip of the needle and is inserted the desired distance into the epidural space.

The proximal end of the catheter is then placed in fluid communication with a source of the anesthetic drug to be introduced. Typically, this is done by securing the proximal end of the catheter within the distal end of an adapter and securing a syringe containing the anesthetic drug to the proximal end of the adapter.

U.S. Pat. No. 4,141,365 discloses a tissue stimulation apparatus for positive positioning of an electrode-bearing lead proximous to tissue which is to be stimulated electrically, the invention particularly includes a body penetration and insertion assembly which carries an elongated flexible strip of physiologically inert plastic material having at least one electrode positioned thereon into contacting relation with said tissue. The insertion assembly comprises a hollow needle having a slot formed longitudinally along the length of one wall thereof, the slot allowing transverse removal of the flexible lead from the needle after proper positioning of the lead and after removal of the needle from the body. The slotted assembly allows use of a flexible electrode lead having electrical connections at the external end thereof which are too large to pass through the hollow needle. U.S. Pat. No. 4,141,365 is incorporated herein by reference in its entirety.

U.S. Pat. No. 4,721,506 discloses an epidural needle and method of use involving a needle shaft having a first end and a second end with an axial channel extending therebetween. The first end of the needle shaft includes an inclined surface and a rounded and blunted point. The second end of the needle includes an attachment means. A solid rod having an inclined surface and a rounded and blunted point is receivable into the axial channel of the needle shaft. When the solid rod is positioned within the axial channel of the needle shaft, the point of the solid rod and the needle together form a unitary tip having an inclined portion and a blunted portion. The blunted portion forms an end face disposed at an angle of about 80 to 100 degrees relative a longitudinal axis of the needle. The unitary tip avoids nicking, piercing, severing, or perforating the veins, arteries, nerves and dura of the patient in traversing the spinal ligaments and in entering a space proximate the dura matter of a spinal cord of a patient to provide liquid communication with the space when the solid rod is withdrawn from the axial channel of the needle. U.S. Pat. No. 4,721,506 is incorporated herein by reference in its entirety.

U.S. Pat. No. 4,808,157 discloses a needle that is a multi-lumen needle and preferably a dual-lumen epidural-spinal needle. The needle is provided with a hub, which allows for attachment of a syringe to one or more of the lumina, or alternatively the attachment of an adapter to which a syringe can be attached. Preferably the lumina have different cross sectional areas. The smaller of the lumina should be of sufficient size to allow a spinal needle, guide wire, or microcatheter to be inserted through the lumen. The larger of the two lumina should preferably be of sufficient size to allow an epidural catheter, spinal needle or guide wire to be introduced. The needle of the present invention has applications of regional anesthesia, chronic and post operative pain management, cricothyroid puncture, intracerebroventricular puncture and, access and drainage of concealed fluid collections within the body. U.S. Pat. No. 4,808,157 is incorporated herein by reference in its entirety.

U.S. Pat. No. 5,425,717 discloses a system for administering epidural anesthesia utilizing an epidural catheter permanently secured at its proximal end to an adapter for putting the catheter in fluid communication with a source of liquid anesthesia. The system employs a splinable needle for inserting the catheter into the peridural space. U.S. Pat. No. 5,425,717 is incorporated herein by reference in its entirety.

U.S. Pat. No. 5,573,519 discloses an elongated, hollow spinal needle that is less prone to causing postdural puncture headache by having a modified, pencil-like point with a rounded shoulder at the juncture between the modified, pencil-like point and the body of the spinal needle. A side port is formed in the hollow needle at a position adjacent the rounded shoulder. The leading edge of the side port is located not more than 1.5 times the external diameter of the hollow needle from the tip of the pencil-like point to reduce the bending moment between the tip and the side port. The cross sectional area of the side port is configured to be equal to or incrementally larger than the cross sectional area of the lumen of the hollow needle. U.S. Pat. No. 5,573,519 is incorporated herein by reference in its entirety.

U.S. Pat. No. 5,628,734 discloses various embodiments of spinal needles, each having a curvature, that are used in a method of administering a spinal anesthetic while preventing the development of post dural puncture headache. U.S. Pat. No. 5,628,734 is incorporated herein by reference in its entirety.

U.S. Pat. No. 5,843,048 discloses an epidural needle through which an epidural catheter may be threaded for administering liquid anesthesia into the epidural space, the needle having a curved distal end, the tip of the needle distal to the opening in the needle shaft being substantially planar at an angle of 80°–100° relative to the curved longitudinal axis of the needle shaft, the needle tip being characterized as being faceted so as to retard inadvertent passage of the needle tip through the dura mater of a patient while at the same time retaining the sharp cutting edges common to a like epidural needle which has not had its tip so treated. U.S. Pat. No. 5,843,048 is incorporated herein by reference in its entirety.

U.S. Pat. No. 5,848,996 discloses a double-hole pencil-point (DHPP) spinal needle that is composed of a closed end blunt ogival or pencil point tip and two circular coaxial holes in close proximity to the tip. Anesthetic solution may be injected through the coaxial holes in a direction parallel to the long axis of the spinal fluid column which allows an even anesthetic distribution with a low dosage required. The spinal needle allows anesthetic solution to be injected even when one of the holes is obstructed by a tissue fragment and rapid reflux of cerebral spinal fluid at twice the rate of single bole pencil point spinal needles. U.S. Pat. No. 5,848,996 is incorporated herein by reference in its entirety.

SUMMARY OF INVENTION

In some embodiments, the invention relates to a needle comprising a hollow shaft having opposed distal and proximal ends, the hollow shaft having a lumen extending from the proximal end of the shaft and terminating at an opening on a top of and proximal to the distal end of the needle shaft. The hollow shaft is adapted to receive an epidural catheter for introducing liquid anesthesia into the patient which can be threaded through the proximal end of the needle until a portion of the catheter exits through the lumen opening on the top of the distal end of the needle shaft; and a cutting surface at the distal end of the hollow shaft adapted to be inserted into a patient, wherein the cutting surface is on the bottom of the distal end of the hollow shaft.

In other embodiments, the invention relates to a method of installing a catheter in the epidural space comprising pushing a needle into the epidural space with a cutting surface of the needle substantially parallel to the dura fibers of the patient, wherein the needle comprises a substantially straight cutting surface, feeding a catheter through the needle and into the epidural space, removing the needle, while holding the catheter stationary, and securing the catheter.

Advantages of the invention may include one or more of the following:

Providing a needle that avoids inadvertent penetration through the dura mater and into the subarachnoid space, causing spinal fluid to leak out;

Providing a needle that avoids the onset of postdural puncture headache;

Providing a needle that limits the number of dural fibers that are cut during use;

Providing a needle that has a cutting edge that is parallel to the dural fibers; and Providing a needle that has an increased sensitivity to the loss of resistance which can be used for detection of the epidural space.

Other aspects and advantages of the invention will be apparent from the following description and the appended claims.

DETAILED DESCRIPTION

The present invention is directed to the straight and curved epidural needles through which a catheter may be introduced into the epidural space for administering anesthesia.

As was mentioned previously, there are two types of needles for use today in administering anesthesia into the epidural space: (1) a needle with a straight shaft for administering the anesthesia from a syringe connected to the proximal end of the needle through a luer fitting; and (2) a needle having a curved distal end for use in introducing a catheter within the epidural space, after which the needle is removed and anesthesia from a syringe is transmitted through the catheter into the epidural space of the patient. The former type needles are on the order of 21–22 gauge; while the latter type are larger, e.g., on the order of 17–18 gauge, in order to accommodate insertion of a catheter within the lumen of the needle shaft (12). The distal end is curved in order to direct the tip of the catheter away from the dura matter so that it may be inserted the desired distance within the epidural space.

The invention may best be understood by reference to the following detailed description taken in conjunction with the accompanying drawings.

Figure 1:
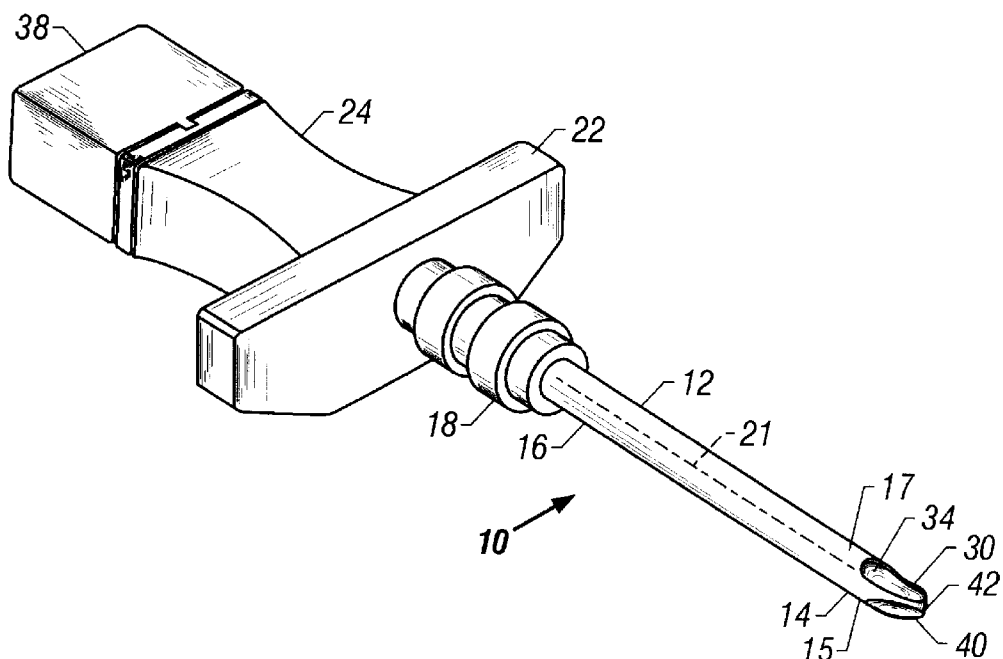
FIG. 1 is a perspective view, greatly enlarged, illustrating a blunted needle in accordance with an embodiment of the invention.
Figure 2:
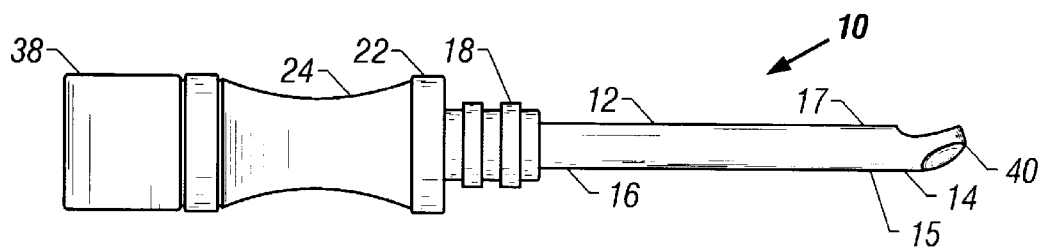
FIG. 2 is a side elevational view of the needle of FIG. 1.

With reference in particular to FIGS. 1–3 and 6, the epidural needle (10) of this embodiment of the invention has a shaft (12), the distal or leading end of which (14) may be curved as seen in FIG. 2, or may be straight (not shown). The proximal end (16) of the shaft (12) is permanently secured to the distal end (18) of a hub (20) of known configuration. The hub (20) has a guide bar (22) for gripping to facilitate introduction and withdrawal of the needle by the anesthetist or other clinician administering the anesthesia.

Figure 3:
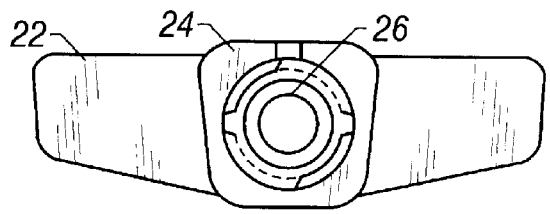
FIG. 3 is a rear view of the needle of FIG. 1 with the solid rod removed.

The proximal end of the hub (24) is provided with a luer fitting (26) as seen in FIG. 3 for securing the needle (10) to a loss of resistance syringe (not shown) prior to introducing the catheter through the needle.

In one embodiment of the invention, the distal end (14) of the needle (10), as seen in FIG. 2 has a top side (17) and a bottom side (15). The cutting surface (40) is located on the bottom side (15), while the opening (30) of the lumen (28) is on the top side (17).

In another embodiment of the invention (not shown), the needle (10) has a first lumen (28) and a second lumen (not shown). The first lumen (28) is adapted to be used with a catheter (44) and/or a stylet (32). The first lumen (28) may have an opening (30) on the on the top (17) of the distal end of the needle (10). The second lumen (not shown) may have an opening (not shown) on the bottom (15) of the distal end of the needle (10). In one embodiment, the opening (not shown) of the second lumen is on the beveled surface (39) at the distal end of the needle (10). In another embodiment, the opening (not shown) of the second lumen is adjacent the cutting surface (40) on the bottom side (15) but slightly towards the top (17) of the needle (10), in either direction from the cutting surface (40). The second lumen is adapted to be used with a spinal needle (not shown) or a pulsating syringe or other known devices to sense the pressure drop in the epidural region.

In another embodiment of the invention (not shown), the needle (10) has a lumen (28) having a first opening (30) on the on the top (17) of the distal end of the needle (10) and a second opening (not shown) on the bottom (15) of the distal end of the needle (10). In one embodiment, the second opening (not shown) of lumen (28) is on the beveled surface (39) at the distal end of the needle (10). In another embodiment, the second opening (not shown) of the lumen (28) is adjacent the cutting surface (40) on the bottom side (15), but slightly towards the top (17) of the needle (10), in either direction from the cutting surface (40). In one embodiment, the second opening may be angled away from the axis (21) of the shaft (12) in order to reduce the incidence of plugging. The second opening is adapted to be used with a spinal needle (not shown) or a pulsating syringe or other known devices to sense the pressure drop in the epidural region. The first opening (30) is adapted to be used with a catheter (44), a stylet (32), and other known devices. The first opening (30) may be on the on the top of the distal end of the needle (10).

The hub may have a lumen (not shown) extending between the proximal and distal ends of the hub and in fluid communication with the lumen (28) in the needle shaft (12).

Figure 6:
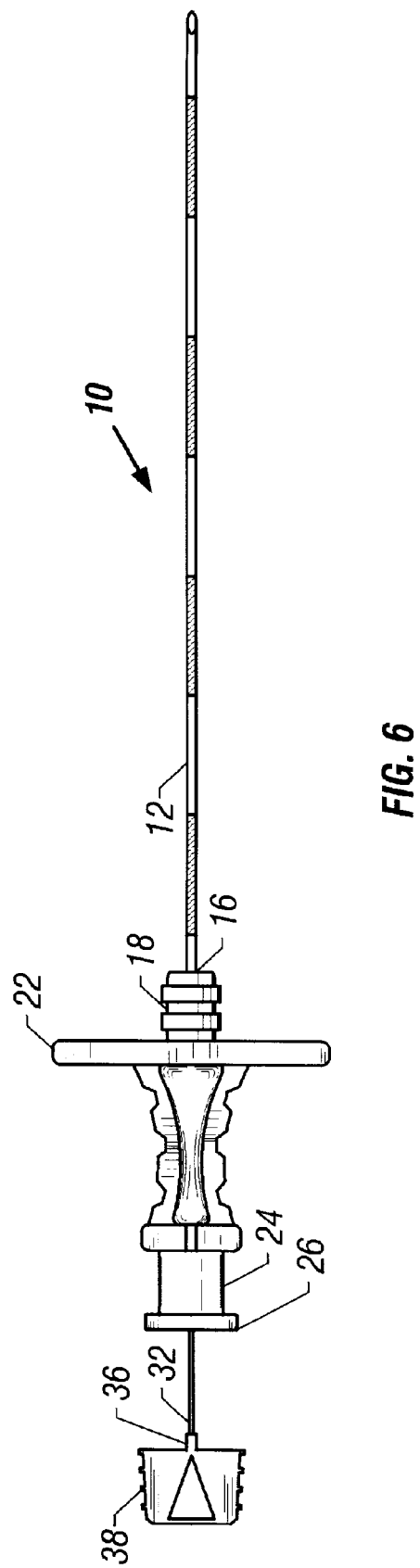
FIG. 6 is a top plan view of the needle in accordance with an embodiment of the invention with the solid rod partially removed from the needle shaft.

As illustrated in FIG. 6, the needle may be provided with a solid or, optionally, semi-rigid plastic stylet (32) which is insertable through the luer fitting (26) at the proximal end of the hub (20) until the handle (38) to which the proximal end of the stylet (32) is secured abuts the proximal end (24) of the hub (20) (as seen in FIGS. 1 and 2), at which time the proximal end (34) of the solid stylet (32) extends to the opening (30) at the distal end of the lumen (28) in the needle shaft (12).

The stylet (32) performs the function with epidural needles of preventing body tissue from blocking or clogging the lumen (28) during penetration of the needle through the tissue of the patient. After the needle (10) has penetrated the tissue, the stylet has served its function and may then be removed, by grasping handle (38) and retracting.

If the needle (10) is a curved epidural needle, e.g., one curved at its distal end (14) as illustrated in FIG. 2, in one embodiment the distal end (14) may be at an angle of 50°–15° relative to the longitudinal axis of the needle shaft (12). In another embodiment, the distal end may be straight (not shown).

On embodiment of the present invention has a cutting surface (40) at the distal end (14) of the needle (10). In one embodiment, the cutting surface (40) may be between parallel and perpendicular to the longitudinal axis (21) of the needle shaft (12); in another embodiment the cutting surface (40) is at an angle of about 10° to about 80° to the longitudinal axis (21) of the needle shaft (12). In another embodiment the cutting surface (40) is at an angle of about 20° to about 60° to the longitudinal axis (21) of the needle shaft (12); and in another embodiment the cutting surface (40) is at an angle of about 30° to about 45° to the longitudinal axis (21) of the needle shaft (12), as seen in FIG. 1.

In one embodiment, the opening (30) of the lumen (28) is substantially free of any cutting surfaces to prevent cutting bodily fibers (not shown) as the needle is inserted. In another embodiment, the edges of the opening (30) of the lumen (28) have been smoothed and/or dulled.

In accordance with the present invention, the distal end (42) of the cutting surface (40) will be distal to the opening (30) of the lumen (28) and in one embodiment, the cutting surface (40) will comprise a length less than about 100% of the needle outside diameter, and in another embodiment less than about 50% of the needle outside diameter. (The needle outside diameter is herein defined as the longest distance between two points on the outer edge of the distal end (14) of the shaft (12).)

Figure 4:
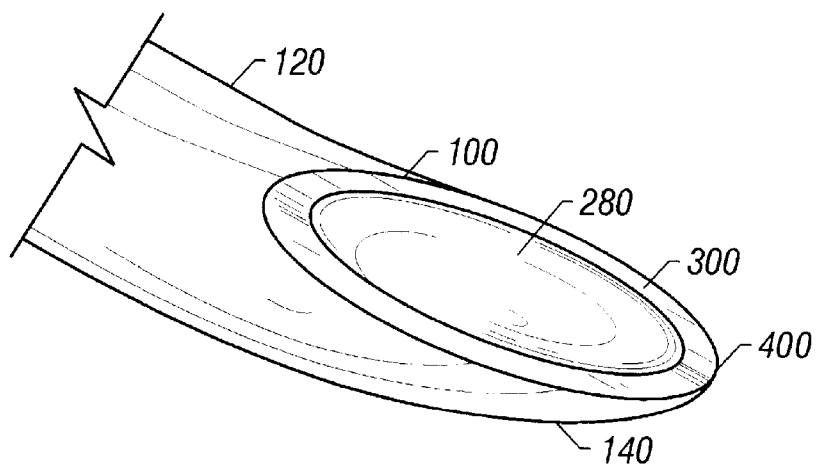
FIG. 4 is a fragmented view illustrating the distal end of a prior art epidural needle.
Figure 5:
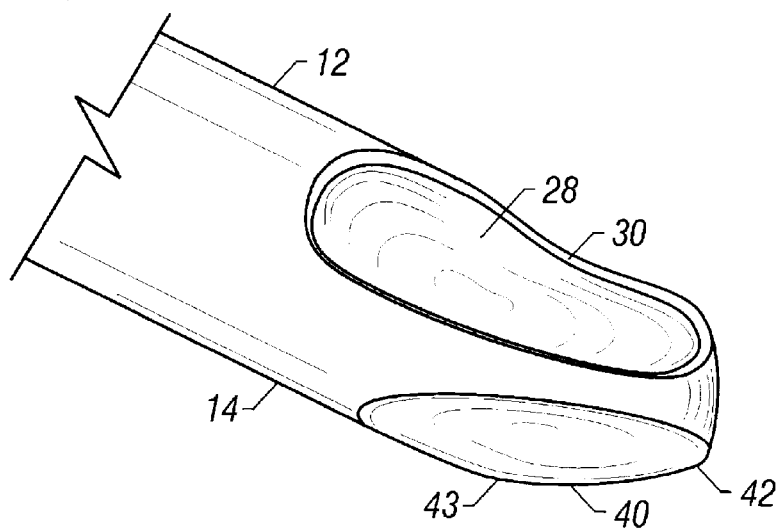
FIG. 5 is a fragmented view similar to FIG. 4 of an epidural needle in accordance with an embodiment of the invention showing the cutting surface and beveled area from the tip of the cutting surface to the lumen.

With reference to FIGS. 4 and 5, some of the differences between a standard Tuohy needle (120) and an embodiment of the needle (10) in accordance with this invention include the following. The needle (10) of this invention has a cutting surface (40) at the distal end (14) of the needle (10). In one embodiment the cuffing surface (40) is substantially linear and substantially straight, and in another embodiment the cutting surface (40) is substantially linear and curved. The proximal end (43) of the cutting surface may begin at the outer edge (41) of the bottom of the needle shaft (12). In one embodiment, the distal end (42) of the cutting surface may end at the most distal point of the distal end (14) of the shaft (12). In another embodiment, the distal end (42) of the cutting surface may end short of the most distal point of the distal end (14) of the shaft (12), and in that embodiment, the distal end (14) of the shaft (12) may be rounded. In one embodiment, the cutting surface (40) comprises a line from a point on the outer edge (41) of the bottom of the needle shaft (12) to the most distal point of the distal end (14) (front of the shaft (12)). In another embodiment, the cutting surface (40) comprises a curve from a point on the outer edge (41) of the bottom of the needle shaft (12) to the most distal point of the distal end (14) (front of the shaft (12)).

In one embodiment, the radial length of the cutting surface (40) is from about 25% to about 90% of the needle outside diameter. In another embodiment, the radial length of the cutting surface (40) is from about 35% to about 70% of the needle outside diameter. In another embodiment, the radial length of the cutting surface (40) is from about 40% to about 60% of the needle outside diameter.

In one embodiment, the axial length of the cutting surface (40) is from about 25% to about 90% of the needle outside diameter. In another embodiment, the axial length of the cutting surface (40) is from about 35% to about 70% of the needle outside diameter. In another embodiment, the axial length of the cutting surface (40) is from about 40% to about 60% of the needle outside diameter. In one embodiment, the axial component of the cutting surface (40) is substantially parallel to the longitudinal axis of the needle (10).

In one embodiment, the axial component of the cutting surface (40) is substantially parallel to the shaft (12) of the needle (10). In another embodiment, the axial component of the cutting surface (40) is within about forty-five degrees of parallel to the shaft (12) of the needle (10) (i.e. plus or minus about forty-five degrees from parallel). In another embodiment, the axial component of the cutting surface (40) is within about thirty degrees of parallel to the shaft (12) of the needle (10) (i.e. plus or minus about thirty degrees from parallel). In a last embodiment, the axial component of the cutting surface (40) is within about fifteen degrees of parallel to the shaft (12) of the needle (10) (i.e. plus or minus about fifteen degrees from parallel).

In one embodiment, the cutting surface (40) approximates the keel of a boat that is from about 0 to about 60 degrees away from parallel with the longitudinal axis of the shaft (12). The proximal end (43) of the cutting surface may begin at the outer edge (41) of the bottom of the needle shaft (12). The distal end (42) of the cutting surface may end at the most distal point of the distal end (14) of the shaft (12).

In another embodiment, needle (10) of this invention has a beveled surface (39) at the distal end (14) of the needle (10). In one embodiment, the beveled surface (39) may be located between the most distal point of the distal end (14) (front of the shaft (12)) and the most distal point of the opening (30) of the lumen (28). In another embodiment, the beveled surface (39) may be located between the distal end of the cutting surface (42) on the bottom of the shaft (12), rounded over the most distal point of the distal end (14) (front of the shaft (12)), and then end at the most distal point of the opening (30) of the lumen (28); in this embodiment, the most distal point of the distal end (14) (front of the shaft (12)) is rounded, and the distal end of the cutting surface (42) is on the bottom of the shaft (12).

In one embodiment, the beveled surface (39) may have a radial length less than about 50% of the needle outside diameter. In another embodiment, the beveled surface (39) may have a radial length less than about 35% of the needle outside diameter. In another embodiment, the beveled surface (39) may have a radial length less than about 25% of the needle outside diameter.

The needle (10) may have a wide range of sharpnesses due to the configuration of the cutting surface (40) in relation to the other components of the needle (10). In one embodiment, the sharpness of the cutting surface (40), as measured by the grams of force required for the needle tip to puncture a sheet of two mil thick polyethylene, is from about 85 grams of force to about 100 grams of force. In another embodiment, the sharpness of the cutting surface, as measured by the grams of force required for the needle tip to puncture a sheet of two mil thick polyethylene, is from about 100 to about 125 grams of force.

Figure 5A:
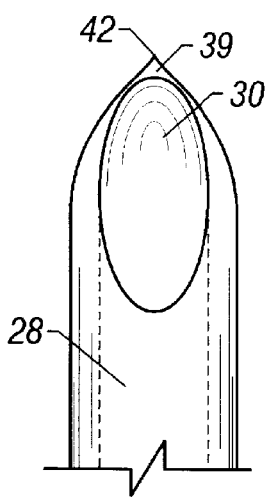
FIG. 5A is an enlarged, fragmentary top elevational view of the tip of the epidural needle of FIG. 5 in accordance with an embodiment of the invention showing the lumen and tip of the cutting surface.
Figure 5B:
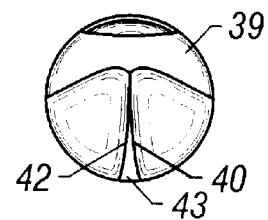
FIG. 5B is a front elevational view showing the cutting surface at the tip of the epidural needle of FIG. 5 in accordance with an embodiment of the invention.
Figure 5C:
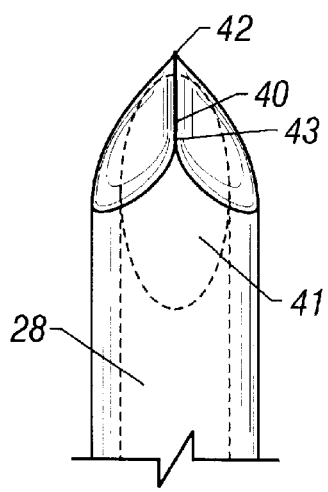
FIG. 5C is a bottom elevational view showing the cutting surface at the tip of the epidural needle of FIG. 5 in accordance with an embodiment of the invention.
Figure 5D:
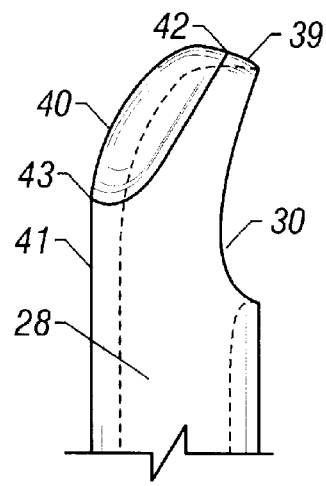
FIG. 5D is a side elevational view showing the cutting surface and the lumen opening at the tip of the epidural needle of FIG. 5 in accordance with an embodiment of the invention.
Figure 5E:
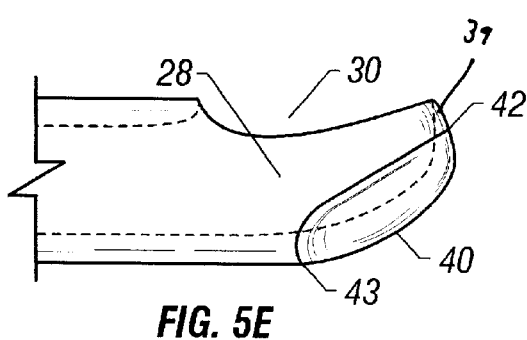
FIG. 5E is a side elevational view showing the cutting surface and the lumen opening at the tip of the epidural needle of FIG. 5 in accordance with an embodiment of the invention.

For clarification, FIG. 5A is a view of the top of the needle (10). The lumen opening (30) is on the top of the needle (10). FIG. 5C is a view of the bottom of the needle (10). The cutting surface (40) extends from its proximal end (43) on the bottom of the needle to its distal end (42) at the front of the needle. FIG. 5B is a view of the front of the needle (10). The front of the needle is its most distal point. The distal end (42) of the cutting surface (40) terminates at the front of the needle. The beveled surface (39) may also be located at the front of the needle (10).

Figure 5F:
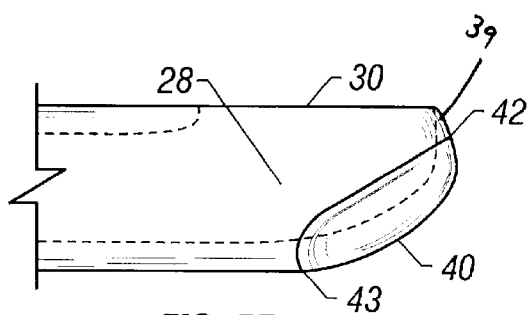
FIG. 5F is a side elevational view showing the cutting surface and the lumen opening at the tip of an epidural needle in accordance with an embodiment of the invention.

FIG. 5F is a side view of another embodiment of the needle (10). The lumen opening (30) is on the top of the needle (10). The cutting surface (40) extends from its proximal end (43) on the bottom of the needle to its distal end (42) at the front of the needle. The distal end (42) of the cutting surface (40) terminates at the front of the needle. The beveled surface (39) may also be located at the front of the needle (10). The opening (30) of the lumen (28) in this embodiment is located substantially even with or substantially aligned with the outside edge of the distal end (14 in FIG. 1) of the shaft (12 in FIG. 1).

The needle (10) of this invention may be employed in any known manner. In one embodiment, the needle (10) is used such that the longitudinal axis of the cutting surface (40) is parallel to the dura fibers (not shown) when the needle is inserted to minimize cutting of the dura fibers and post dural puncture headaches.

If the needle (10) is inserted until it abuts the ligmentum flavum, the stylet (32) may be removed, and the needle may be connected to a loss of resistance syringe, as described earlier, the needle may then be advanced into the epidural space. At this point, the syringe may be disconnected from the needle and the anesthetist is now ready to insert the catheter for introducing anesthesia into the epidural space, as will now be described.

Figure 7:
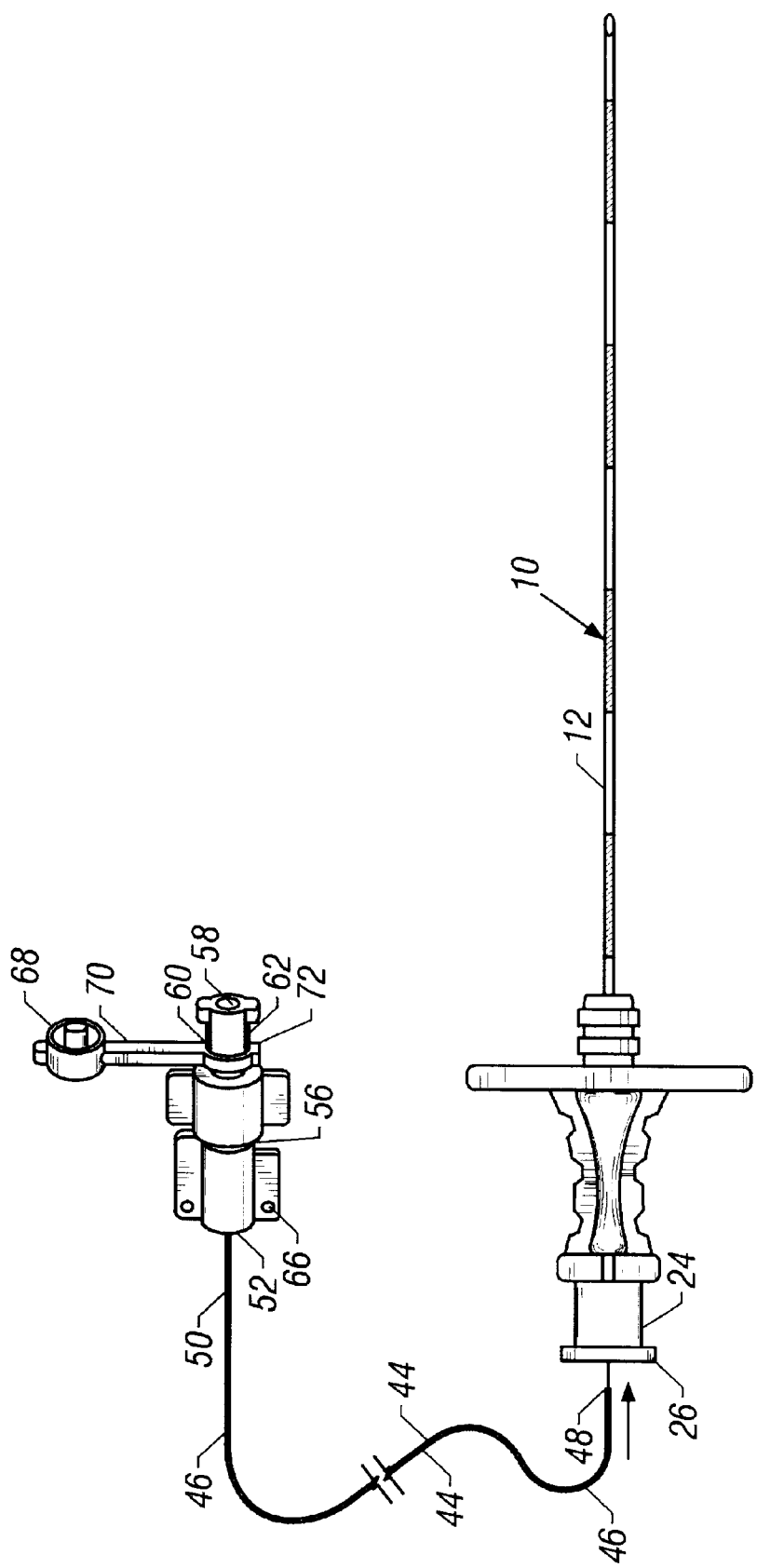
FIG. 7 is a schematic view illustrating the use of the epidural needle in accordance with an embodiment of the invention in combination with an epidural catheter to administer anesthesia.

With reference to FIG. 7, a catheter (44) is shown to comprise a cannula (46) having opposed distal and proximal ends (48) and (50) respectively. The Distal end (46) is inserted within the proximal end (24) of the needle hub (20) and advanced until the distal end (48) of the cannula is inserted the desired distance within the epidural space. The needle may then be carefully withdrawn from the patient over the catheter.

The proximal end (50) of the catheter (44) is releasably secured to the distal end (52) of an adapter (56) having a hollow bore (58) extending from the distal end (52) to the proximal end (60) of the adapter. The proximal end of the adapter has a syringe port or luer fitting (62) for securing the adapter to a syringe or other source of liquid anesthesia. In one embodiment, the adapter (56) is provided with a finger grip flange (64) having holes (66) for securing the adapter to the patients gown or other item and a cap (68) fitable within the syringe port (62), the cap (68) being secured to the adapter by linkage (70) and retaining ring (72). The purpose of the cap is to close off the syringe port when not in use administering anesthesia.

In accordance with this invention, the anesthesia may be administered in any known manner. For example, in one embodiment, following the procedure previously described, the needle may be inserted within the epidural space. The catheter is then threaded through the needle until a desired length of the catheter is within the epidural space, after which the needle is then removed by sliding it over the entire length of catheter, care of course being taken not to dislodge the position of the catheter within the epidural space. After the needle has been removed, the proximal end of the catheter is then secured to the adapter in preparation for the commencement of the administration of anesthesia.

In one embodiment, the needle (10) has a generally circular cross-section. In another embodiment, the needle (10) has a non-circular cross-section, for example, oval, rectangular, diamond, square, triangular, etc. In one embodiment, the lumen (28) has a non-circular cross-section, for example, oval, rectangular, diamond, square, triangular, etc., where the non-circular lumen (28) is adapted to be used with a corresponding catheter (44) or other device having a non-circular cross-section. In another embodiment, the combination of a non-circular catheter (44) and a non-circular lumen (28) may be used to guide the catheter (44) within the epidural space.

It will be appreciated that various changes may be made with out departing from the spirit of the present invention, the scope of which will be defined in the appended claims.

For example, as shown in FIGS. 6 and 7, to assist the anesthetist in determining the proper distance to insert the needle for a given patient, the needle shaft (12) may be provided with needle depth markings consisting of alternating sections of a different color of a desired uniform length, e.g. one centimeter. If desired, each segment may also be numbered consecutively, the number on each segment designating the distance of that segment within the body.

It is also contemplated the present invention may useful as a split needle wherein the needle may be removed from the catheter by splitting it along the shaft (12) instead of having to slide it over the needle, thereby permitting the proximal end of the catheter to be permanently secured to an adapter.

In one embodiment, epidural needle (10) is part of a kit (not shown) that may include a spinal needle (not shown), a catheter assembly (44), a hub (24), and a stylet (32) to occlude the lumen (28) of the epidural needle (10) and placed in a package (not shown). Kit (not shown) may also include a stylet (not shown) for spinal needle (not shown). Kit (not shown) may also include other items (not shown) in addition to spinal needle (not shown) and stylet (not shown), such as gloves, skin preparation materials, medicaments and the like for particular applications. In one embodiment, package (not shown) may be formed from materials substantially resistant to microorganisms, sealed and exposed to conditions suitable to render any microorganisms therein non-viable. Suitable materials for forming package (not shown) include but are not limited to thermoplastic films, metallic foils, paper, non-wovens as well as combinations of these materials. Suitable conditions for rendering microorganisms non-viable include, but are not limited to, exposure to gaseous agents such as ethylene oxide, vapor phase hydrogen peroxide and the like, and exposure to ionizing radiation such as is generated by electron beam, ultraviolet or gamma radiation.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. In an epidural needle comprising a hollow shaft having opposed distal and proximal ends, the distal end having a cutting surface for insertion into a patient's epidural space, the needle shaft having a lumen extending from the proximal end of the needle shaft and terminating at an opening on the top of the distal end of the needle shaft and configured to allow an epidural catheter for introducing liquid anesthesia into the patient to be threaded through the proximal end of the needle until a portion of the catheter exits through the opening in the needle shaft;

the improvement comprising the cutting surface, wherein the cutting surface is on the bottom of the distal end of the hollow shaft.

2. The epidural needle of claim 1 wherein the cutting surface is from the bottom of the distal end of the hollow shaft to the front of the distal end of the hollow shaft.

3. The epidural needle of claim 1 wherein the needle is adapted to be used where the cutting surface is substantially parallel to the dural fibers, so as to minimize dura cutting and post dural puncture headaches.

4. The epidural needle of claim 1 wherein the sharpness of the cutting surface, as measured by the grams of force required for the needle tip to puncture a sheet of two mil thick polyethylene, is from about 85 grams of force to about 100 grams of force.

5. The epidural needle of claim 1 wherein the sharpness of the cutting surface, as measured by the grams of force required for the needle tip to puncture a sheet of two mil thick polyethylene, is from about 100 to about 125 grams of force.

6. The needle of claim 1 wherein the needle is a 17 or 18 gauge needle.

7. A needle comprising:

a hollow shaft having opposed distal and proximal ends, the hollow shaft having a lumen extending from the proximal end of the shaft and terminating at an opening on a top of and proximal to the distal end of the needle shaft; and a cutting surface at the distal end of the hollow shaft adapted to be inserted into a patient, wherein the cutting surface is on the bottom of the distal end of the hollow shaft.

8. The needle of claim 7 wherein the cutting surface begins on the bottom of the distal end of the hollow shaft and ends on the front of the distal end of the hollow shaft.

9. The needle of claim 7 further comprising:

a solid rod having opposed proximal and distal ends, the distance between the opposed ends of the solid rod being substantially the same as the distance between the proximal end of an adapter attached to the needle and the distal tip of the needle shaft, the proximal end of the solid rod being secured to a gripping means for holding the rod, the rod being insertable through the proximal end of the adapter such that when the gripping means abuts the proximal end of the adapter, the distal end of the rod extends within the opening in the needle shaft, wherein the rod is adapted to prevent tissue debris from clogging the lumen during introduction of the needle into a patient's body.

10. The needle of claim 9 solid rod comprises a semi-rigid plastic material.

11. The needle of claim 7 further comprising a beveled surface, wherein the beveled surface is rounded and extends from the distal end of the cutting surface on the bottom of the shaft to the opening of the lumen on the top of the shaft.

12. The needle of claim 11 wherein the beveled surface has a radial length less than about 25% of the needle outside diameter.

13. The needle of claim 7 wherein the cutting surface is substantially linear and substantially straight.

14. The needle of claim 7 wherein the cutting surface is substantially linear and curved.

15. The needle of claim 7 wherein the cutting surface has the shape of a hull and extends from the outer edge of the bottom of the needle shaft to the front of the distal end of the shaft.

16. The needle of claim 7 wherein the axial component of the cutting surface is within about thirty degrees of parallel to the longitudinal axis of the shaft.

17. A method of installing a catheter in the epidural space comprising:
   (a) pushing a needle into the epidural space with a cutting surface of the needle substantially parallel to the dura fibers of the patient, wherein the needle comprises a substantially straight cutting surface;
   (b) feeding a catheter through the needle and into the epidural space;
   (c) removing the needle, while holding the catheter stationary; and
   (d) securing the catheter.

18. The method of claim 17 wherein the cutting surface of the needle comprises an axial component that is within about thirty degrees of parallel to the longitudinal axis of the shaft of the needle.

19. An epidural needle kit comprising:
   an epidural needle;
   a lumen through the epidural needle having a end on a top surface of a distal end of the needle;
   a stylet adapted to fit inside the lumen of the epidural needle;
   a catheter adapted to fit inside the lumen of the epidural needle; and
   a hub adapted to connect to a proximal end of the epidural needle;
   the improvement comprising a cutting surface on the epidural needle, wherein the cutting surface is on a bottom surface of the distal end of the needle.

20. The epidural needle kit of claim 19 further comprising a spinal needle adapted to fit inside the lumen of the epidural needle.

* * * * *